United States Patent [19] [11] 4,071,564

Bauer et al. [45] Jan. 31, 1978

[54] PROCESS FOR THE PRODUCTION OF 2-ALKOXY-4-ALKENYL PHENOLS

[75] Inventors: Kurt Bauer, Holzminden; Reiner Mölleken, Golmbach Ortsteil Warbsen; Fritz Exner, Holzminden, all of Germany

[73] Assignee: Haarmann & Reimer Gesellschaft mit beschrankter Haftung, Holzminden, Germany

[21] Appl. No.: 568,090

[22] Filed: Apr. 14, 1975

[30] Foreign Application Priority Data

Apr. 19, 1974 Germany ............................ 2418972

[51] Int. Cl.$^2$ ............................................ C07C 41/00

[52] U.S. Cl. ........................... 260/613 D; 260/613 R; 252/522

[58] Field of Search ........... 260/613 R, 613 D, 624 H

[56] References Cited

U.S. PATENT DOCUMENTS

| | | | |
|---|---|---|---|
| 2,414,385 | 1/1947 | Milas | 260/613 R X |
| 2,422,171 | 6/1947 | Saunders | 260/624 H X |
| 2,430,002 | 11/1947 | DeGroote et al. | 260/619 A X |
| 2,497,503 | 2/1950 | Jones | 260/624 H X |
| 2,979,534 | 4/1961 | Petropoulos et al. | 260/624 H X |

OTHER PUBLICATIONS

Grant, The Condensed Chemical Dictionary, Eighth Ed., (1971), p. 483.

Kakhniashvili et al., Chemical Abstracts, vol. 61, (1964), 8214.

*Primary Examiner*—Bernard Helfin
*Attorney, Agent, or Firm*—Burgess, Dinklage & Sprung

[57] ABSTRACT

The invention concerns new 2-alkoxy-4-alkenyl phenols of the formula

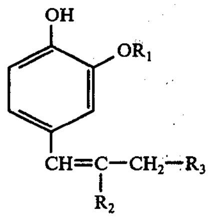

wherein $R_1$ is methyl or ethyl and $R_2$ and $R_3$ are different from one another and mean hydrogen or methyl;

a process for the preparation of said 2-alkoxy-4-alkenyl phenols comprising condensing 2-alkoxy phenols with butyraldehyde or isobutyraldehyde in the presence of an acid catalyst and thermal splitting the condensation product in the presence of a catalyst; and the use of the new 2-alkoxy-4-alkenyl phenols as odorants.

11 Claims, No Drawings

PROCESS FOR THE PRODUCTION OF 2-ALKOXY-4-ALKENYL PHENOLS

The invention relates to new 2-alkoxy-4-alkenyl phenols, to a process for their production and their use as odorants.

The new 2-alkoxy phenols correspond to the general formula:

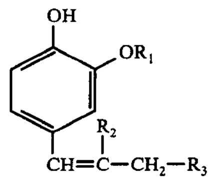

(I)

in which $R_1$ represents a methyl or ethyl radical whilst $R_2$ and $R_3$, which are different from one another, each represent hydrogen or a methyl radical.

The following compounds fall within the scope of the general formula (I): 1-(4-hydroxy-3-ethoxy phenyl)-1-butene, 1-(4-hydroxy-3-methoxy phenyl)-1-butene, 1-(4-hydroxy-3-methoxy phenyl)-2-methyl-1-propene and 1-(4-hydroxy-3-ethoxy phenyl)-2-methyl-1-propene.

A process for the production of compounds corresponding to the formula (I) has been found, being distinguished by the fact that, in a first stage, phenol derivatives corresponding to the general formula (II) are reacted in the presence of acid catalysts with aldehydes corresponding to the general formula (III):

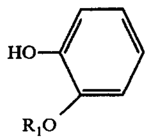

(II)

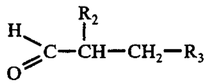

(III)

and the product of condensation formed in the first stage is split in a second stage by heating in the presence of a preferably basic catalyst to form the required compound of general formula (I).

Accordingly, suitable starting materials for the first stage of the process according to the invention are the phenol derivatives 1-hydroxy-2-methoxy and 1-hydroxy-2-ethoxy benzene, whilst butyraldehyde and isobutraldehyde may be used as the aldehydes.

Acid catalysts suitable for use in the condensation reaction include medium-strength to strong proton acids, acidic ion exchangers, acid anhydrides of inorganic acids or Lewis acids: for example strong to medium-strength inorganic acids, strong organic acids, Lewis acids or inorganic and organic ion exchangers or solid acid anhydrides of strong inorganic, non-oxidising acids.

The following are mentioned as examples of strong to medium-strength inorganic acids: sulphuric acid, phosphoric acids such as, for example orthophosphoric acid, pyrophosphoric acid, metaphosphoric acid, polyphosphoric acid, phosphortungstic acid or phosphormolybdic acid, hydrochloric acid, hydrofluoric acid, hydrobromic acid and amidosulphonic acid.

The following are examples of strong organic acids: organic sulphonic acids such as, for example p-toluene sulphonic acid, p-methoxy phenyl sulphonic acid, oxalic acid, trifluoroacetic acid and picric acid.

The following are mentioned as examples of inorganic ion exchangers: natural hydrosilicates of aluminium such as, for example, montmorillonites, glauconites or zeolites, prepared (for example by acid treatment) hydrosilicates of aluminum (cf. Ullmanns Enzyklopadie der technischen Chemie, vol. 8, Third Edition 1957, page 801), mineral cation exchangers produced on a commercial scale from silicates, for example kaolin or feldspar, and alumina minerals, for example bauxite, and silica and sodium hydroxide or soda (cf. Ullmann, Vol. 8, Third Edition, 1957, page 802), the aluminium compounds also being replaceable either wholly or in part by iron, tin, lead, zirconium, titanium, chromium, tungsten, vanadium or boron compounds (cf. Ullmann, Vol. 8, Third Edition 1957, page 802), or carbon-based exchangers activated with sulphuric acid. Organic ion exchangers are, for example, polycondensation resins based on phenol-formaldehyde or polymerisation resins based on styrene or styrenes containing carboxyl or phosphoric acid groups and substituted by alkyl, alkoxy or halogen groups, and also copolymers of styrene, acrylic acid, methacrylic acid or maleic acid containing sulphonic acid, carboxyl or phosphoric acid groups (cf. Ullmann, Vol. 8, Third Edition 1957, pages 806–810).

The following are mentioned as examples of Lewis acids: aluminium chloride, antimony trichloride, antimony pentachloride, iron(III)chloride, boron fluoride, zinc chloride or phosphorus halides.

Phosphorus pentoxide is mentioned as an example of a solid acid anhydride of a non-oxidising inorganic acid.

It is also possible to use mixtures of the above-mentioned catalysts.

The temperatures for the first stage of the reaction are generally in the range of from 0° to 100° C, preferably in the range of from 60° to 90° C and, with particular preference, in the range of from 65° to 85° C. Basically, the pressure applied is not critical. In general, the reaction is carried out under normal pressure although in special circumstances it may be advantageous to work under reduced pressure or excess pressure. In cases where the reaction is carried out under reduced pressure, the degree of reaction can be increased by continuously removing the water formed during the reaction, whilst in cases where the reaction is carried out under excess pressure the reaction velocity may be increased by simultaneously increasing the reaction temperature.

The phenol derivative is generally used in excess. For example, it is advantageous to react about 3 to 10 mols of the phenol derivative with 1 mol of aldehyde. The unreacted excess of the phenol derivative may readily be separated off from the condensation product formed, for example by distillation.

High yields of the corresponding bisphenol are formed as a condensation product in the first stage of the process according to the invention from 2 molecules of the phenol derivative and 1 molecule of aldehyde, the H-atom of the benzene nucleus in the p-position to the hydroxyl group preferably being substituted by the carbonyl carbon atom of the aldehyde. The reaction scheme is illustrated by way of example below with reference to the reaction of 1-hydroxy-2-methoxy benzene with butyraldehyde:

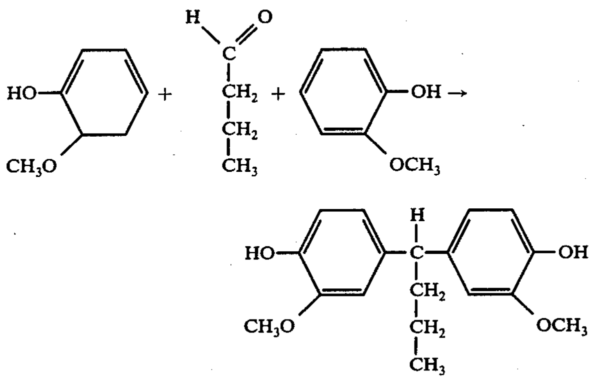

Accordingly, the following bisphenols may be formed as condensation products in the first stage of the process according to the invention: 1,1-bis-(4-hydroxy-3-methoxy phenyl)-butane, 1,1-bis-(4-hydroxy-3-ethoxy phenyl)-butane, 1,1-bis-(4-hydroxy-3-methoxy phenyl)-2-methyl propane and 1,1-bis-(4-hydroxy-3-ethoxy phenyl)-2-methyl propane.

In the second stage, the condensation product obtained in the first stage is subjected to thermal splitting at 150° to 300° C in the presence of a catalyst.

The following are mentioned as examples of catalysts suitable for use in the thermal splitting stage of the process according to the invention: alkali and alkaline earth metals, and also aluminium, zinc, cadmium or lead. However, it is preferred to use basic catalysts, for example the oxides, hydroxides, alcoholates, phenolates, alkyl carboxylates, carbonates, amides or hydrides of the above-mentioned metals, especially the alkali and alkaline earth metals. The alkali metal hydroxides, lithium, sodium and, in particular, potassium hydroxide, have proved to be particularly suitable basic catalysts.

It is also possible to use mixtures of the above-mentioned catalysts. The catalysts are generally used in quantities of from about 0.01 to 10% by weight and preferably in quantities of from about 0.1 to 5% by weight, based on the condensation product used.

The reaction temperatures required for splitting are generally in the range of from 150° to 300° C. In cases where the above-mentioned alkali compounds are used, it is necessary to apply, for example, relatively low reaction temperatures in the range of from 150° to 260° C, whereas reaction temperatures in the range of from 200° to 300° C are generally required in the case of other catalysts. The preferred temperature range for thermal splitting is from 200° to 260° C.

Splitting of the bisphenols may be carried out under normal pressure or under reduced pressure, a reduced pressure of from about 0.1 to 700 mm Hg generally being maintained in dependence upon temperature. It has proved to be particularly advantageous to maintain a reduced pressure of 0.1 to 100 mm Hg, for example at temperatures in the range from 200° to 260° C.

To carry out the process according to the invention, the condensation product from the first stage may be heated together with the catalyst and the required product, together with the 1-hydroxy-2-methoxy or 1-hydroxy-2-ethoxy benzene simultaneously split off, may be distilled off from the mixture in a simple manner. Surprisingly it is only the 1,1-bis-(4-hydroxy-3-alkoxy phenyl)-alkanes which are split during the splitting reaction, whereas the compounds substituted in the ortho- or meta-position which accumulate as secondary products during the condensation reaction are not split during the splitting reaction to form the corresponding ortho- or meta-alkenyl phenol derivatives. Separation of the product mixture obtained is preferably carried out by recrystallisation from solvents, for example alcohols such as methanol and ethanol, hydro-carbons such as ligroin, cyclohexane, benzene, toluene and xylene, ethers such as methyl ether, or water or mixtures thereof, or by fractional distillation.

The formula (I) compounds according to the invention are valuable odorants which add a new range of nuances to known clove odorants, for example of the isoeugenol and ethyl isoeugenol type. By comparison with conventional clove odorants, they have smoky, sweet-vanillin-like odour notes reminiscent of oakmoss-leather, providing perfume manufacturers with new, interesting possibilities for perfume compositions. For example, the odour of 1-(4-hydroxy-3-ethoxy phenyl)-1-butene and 1-(4-hydroxy-3-ethoxy phenyl)-2-methyl-1-propene, is softer and more flowery and sweet than that of isoeugenol, so that these compounds may be used with advantage, for example, in perfume compositions where the powdery-spicey clove note of isoeugenol is undesirable. 1-Hydroxy-3-methoxy phenyl)-1-butene is particularly characterised by soft, flowery-sweet and hard, mossy leather-like components. In 1-(4-hydroxy-3-methoxy phenyl)-2-methyl-1-propene, powdery, spicey, clove-like and smoky, guaiacum-wood-like components are combined in the odour complex of a single compound, which provides for a completely uniform odour combination throughout the entire vaporisation process and precludes any differences in the way the complex disintegrates with time. Combinations of this kind may be used with advantage, for example in mens perfumes, All Spice, Fougère.

EXAMPLE 1

72 g (1 mol) of butyraldehyde were added dropwise over a period of 1 hour at 70° C to 2670 g (19.35 mol) of guaethol (1-hydroxy-2-ethoxy benzene) and 214 g of anhydrous cation exchanger in the H-form (Lewatit ®SC 102/$H^+$). The mixture was stirred for a further 3 hours at 70° C, after which the water formed and the unreacted butyraldehyde were distilled off from the reaction mixture at a sump temperature of at most 70° C/10 mm Hg. Another 72 g (1 mol) of butyraldehyde were added to the remaining mixture over a period of 1 hour. After stirring for 2 hours at 70° C, the liquid phase of the reaction mixture was filtered off from the ion exchanger and the unreacted butyraldehyde and excess guaethol were separated off by distillation (110° C/10 mm Hg), leaving 383 g of a condensation product of guaethol and butyraldehyde (consisting essentially of 1,1-bis-(4-hydroxy-3-ethoxy phenyl)-butane). Following the addition of 400 mg of NaOH, 377 g of this condensation product were heated in a distillation apparatus with a 10 cm Vigreux column attachment. A mixture of guaethol and 1-(3-ethoxy-4-hydroxy phenyl)-1-butene distilled off at a sump temperature of 200° to 260° C/10 mm Hg. A total of 270 g of the required product of splitting were obtained, 1-(3-ethoxy-4-hydroxy phenyl)-1-butene being isolated therefrom in pure form by fractional distillation at 142° - 144° C/10 mm Hg. The yield amounted to 134.8 g (= 61.5% of the theoretical yield based on the condensation product used). Assessment of odour: clove odorant with a sweet, soft flowery note, less powdery-spicey by comparison with isoeugenol.

EXAMPLE 2

72 g (1 mol) of butyraldehyde were added dropwise over a period of 1 hour at 58° C to 2604 g (21 mols) of guaiacol (1-hydroxy-2-methoxy benzene) and 200 g of an anhydrous cation exchanger in the H-form (Lewatit ® SC 102/H+). The mixture was then stirred for a further 2 hours at 70° C, and the water formed during the reaction and the unreacted butyraldehyde were distilled off from the reaction mixture at a sump temperature of at most 60° C/10 mm Hg. Another 144 g (2 mols) of butyraldehyde were added to the mixture. After stirring for 2 hours at 58° C, the liquid phase of the reaction mixture was filtered off from the ion exchanger and the unreacted butyraldehyde and excess guaiacol were separated off by distillation (100° C/10 mm Hg), leaving 612 g of a condensation product of guaiacol and butyraldehyde (consisting essentially of 1,1-bis-(4-hydroxy-3-methoxy phenyl)-butane 2750 g of this condensation product were heated in a distillation apparatus following the addition of 3 g of KOH. A mixture of guaiacol and 1-(4-hydroxy-3-methoxy phenyl)-1-butene distilled off a sump temperature of 220° to 260° C/10 mm Hg. A total of 1978 g of the required product of splitting were obtained, 1-(4-hydroxy-3-methoxy phenyl)-1-butene being isolated therefrom in pure form by fractional distillation at 139° - 141° C/10 mm Hg. The yield amounted to 1182 g (= 72.9% of the theoretical yield based on the condensation product used). Assessment of odour: sweet-flowery with a hard, masculine nuance somewhat reminiscent of oakmoss.

EXAMPLE 3

2604 g (21 mols) of guaiacol (1-hydroxy-2-methoxy benzene) and 100 g of an anhydrous cation exchanger (Lewatit SC 102/H+) in the H form were initially introduced, followed by the successive addition over a period of 30 minutes in each case at a temperature of 80° C of 3 × 72.1 g (1 mol) portions of isobutyraldehyde. After each batch of the aldehyde had been added, the reaction mixture was stirred for 30 minutes and the water formed was distilled off. Distillation was stopped at 60° C/10 mm Hg in each case.

Thereafter the liquid phase of the reaction mixture was filtered off from the ion exchanger, and the unreacted isobutyraldehyde and excess guaiacol were separated off by distillation (100° C, 10 mm Hg), leaving 359 g of a condensation product of guaiacol and isobutyraldehyde (consisting essentially of 1,1-bis-(4-hydroxy-3-methoxy phenyl)-2-methyl propane). 359 g of this condensation product were heated in a distillation apparatus following the addition of 400 mg of NaOH. A mixture of guaiacol and 1-(4-hydroxy-3-methoxy phenyl)-2-methyl-1-propene distilled off at a sump temperature of 200° - 260° C/10 mm Hg. A total of 271 g of the product of splitting were obtained, 1-(4-hydroxy-3-methoxy phenyl)-2-methyl-1-propene being isolated therefrom in pure form by fractional distillation at 121° C/5mm Hg. The yield amounted to 134.5 g (= 67.8% of the theoretical yield, based on the condensation product used). Assesssment of odour: powdery-spicey reminiscent of cloves and of guaiacum wood and glycine.

EXAMPLE 4

2900 g (21 mols) of guaethol (1-hydroxy-2-ethoxy benzene) and 200 g of an anhydrous cation exchanger (Lewatit ®SC 102/H+in the H-form were initially introduced, followed by the successive addition over a period of 30 minutes in each case at a temperature of 80° C of 3 × 72.1 g (1 mol) portions of isobutyraldehyde. After each batch of the aldehyde had been added, the reaction mixture was stirred for 30 minutes and the water formed during the reaction was distilled off. Distillation was stopped at 60° C/10 mm Hg in each case. Thereafter the liquid phase of the reaction mixture was filtered off from the ion exchanger and the unreacted isobutyraldehyde and excess guaethol were separated off by distillation (110° C/10 mm Hg), leaving 220.7 g of the condensation product of guaethol and isobutyraldehyde (consisting essentially of 1,1-bis-(4-hydroxy-3-ethoxy phenyl)-2-methyl propane). 220.7 g of this condensation product were heated in a distillation apparatus following the addition of 200 mg of NaOH. A mixture of guaethol and 1-(3-ethoxy-4-hydroxy phenyl)-2-methyl-1-propene distilled off at a sump temperature of 200° - C/10 mm Hg. A total of 161 g of the product of splitting were obtained, 1-(3-ethoxy-4-hydroxy phenyl)-2-methyl-1-propene being isolated therefrom in pure form by fractional distillation at b.p. 129° - 130° C/5 mm Hg. The yield amounted to 83.1 g (= 64.7% of the theoretical yield, based on the condensation product used). Assessment of odour: sweet, soft-flowery reminiscent of orchids and somewhat of vanilla, but less heavy and balsamy than vanilla.

We claim:

1. A process for the production of 2-alkoxy-4-alkenyl phenols of the formula

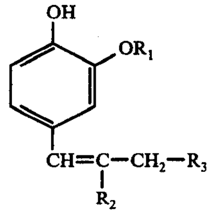

in which $R_1$ is methyl or ethyl whilst $R_2$ and $R_3$ which are different from one another, are hydrogen or methyl comprising reacting in a first stage 2-alkoxy phenols of the formula

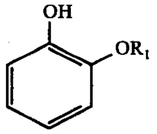

in which $R_1$ has the meaning given above with butyraldehyde or isobutyaraldehyde at a temperature from 0° to 100° C in the presence of an acid catalyst selected from the group consisting of sulphuric acid, hydrochloric acid, phosphoric acid, pyrophosphoric acid, sulphonic acid and acidic inorganic or organic ion exchangers and subsequently thermally splitting the condensation product obtained in a second stage by heating it at a temperature from 150° to 300° C in the presence of a basic catalyst selected from the group consisting of alkali or alkaline earth metals, aluminium, zinc, cadmium and lead and the oxides, hydroxides, alcoholates, phenolates, alkyl carboxylates, carbonates, amides or hydrides of the aforementioned metals.

2. The process of claim 1, wherein an oxide or hydroxide of an alkali or alkaline-earth metal is used as basic catalyst.

3. The process of claim 1, wherein the water formed during the condensation reaction is distilled off in the first stage.

4. Process of claim 1 wherein $R_1$ is ethyl, $R_2$ is hydrogen, and $R_3$ is methyl and the 2 alkoxyphenol is reacted with butyraldehyde.

5. Process of claim 1, wherein $R_1$ is methyl, $R_2$ is hydrogen, and $R_3$ is methyl and the 2 alkoxyphenol is reacted with butyraldehyde.

6. Process of claim 1, wherein $R_1$ is methyl, $R_2$ is methyl, and $R_3$ is hydrogen and the 2 alkoxyphenol is reacted with isobutyraldehyde.

7. Process of claim 1, wherein $R_1$ is ethyl, $R_2$ is methyl, and $R_3$ is hydrogen and the 2 alkoxyphenol is reacted with isobutyraldehyde.

8. Process of claim 1, wherein before the thermal splitting, the acid catalyst is removed and thereafter the basic catalyst is added.

9. Process of claim 8, wherein the acid catalyst is an ion exchanger.

10. Process of claim 1, wherein isomers of the condensation product are formed in the condensation, and only said 2-alkoxy-4-alkenyl phenols are formed in said splitting.

11. Process of claim 1, wherein the thermal splitting is performed in the liquid phase.

* * * * *